United States Patent [19]

Parker, Jr. et al.

[11] Patent Number: 4,930,352

[45] Date of Patent: Jun. 5, 1990

[54] REFLECTIVE MEMBRANE OPTICAL SCINTILLATOR

[75] Inventors: Jack H. Parker, Jr.; Mark L. DeLong, both of Kettering, Ohio

[73] Assignee: The United States of America as represented by the Secretary of the Air Force, Washington, D.C.

[21] Appl. No.: 330,840

[22] Filed: Mar. 30, 1989

[51] Int. Cl.$^5$ .............................................. G01M 7/00
[52] U.S. Cl. ..................................... 73/662; 73/866.4
[58] Field of Search ............. 73/655, 668, 662, 866.4; 367/140; 356/244; 434/1

[56] References Cited

U.S. PATENT DOCUMENTS

| | | | |
|---|---|---|---|
| 4,310,905 | 1/1982 | Palmer | 367/140 |
| 4,833,928 | 5/1989 | Luukkala et al. | 73/655 |

Primary Examiner—Hezron E. Williams
Assistant Examiner—Louis M. Arana
Attorney, Agent, or Firm—Bobby D. Scearce; Donald J. Singer

[57] ABSTRACT

A reflective membrane optical scintillator system for laboratory simulation of atmospheric laser scintillation is described which comprises a substantially rigid frame defining an opening of preselected size and shape, a reflective membrane stretched on the frame within the opening and held to provide a well defined boundary for vibrational excitation of the membrane, a source of light and related optics for directing a collimated light beam onto the membrane, and an acoustic transducer for controllably vibrationally exciting the membrane with a preselected acoustical spectrum for spatially modulating the beam whereby atmospheric turbulence effects are predictably simulated.

8 Claims, 8 Drawing Sheets

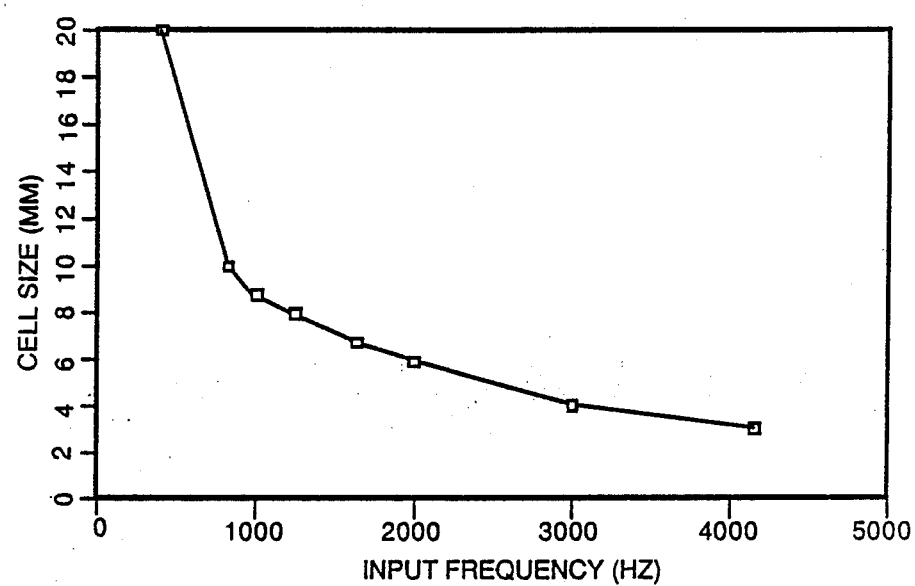
Fig. 5
Fig. 7a
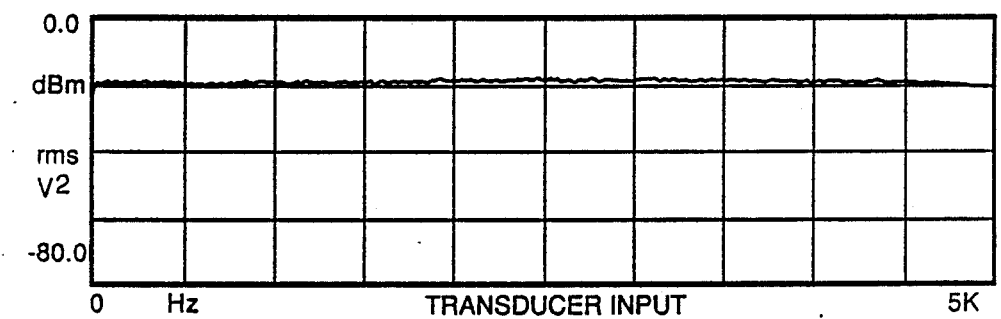
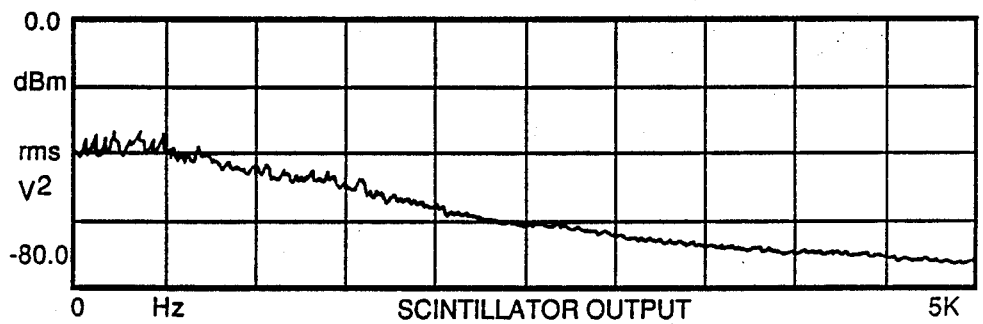
Fig. 7b

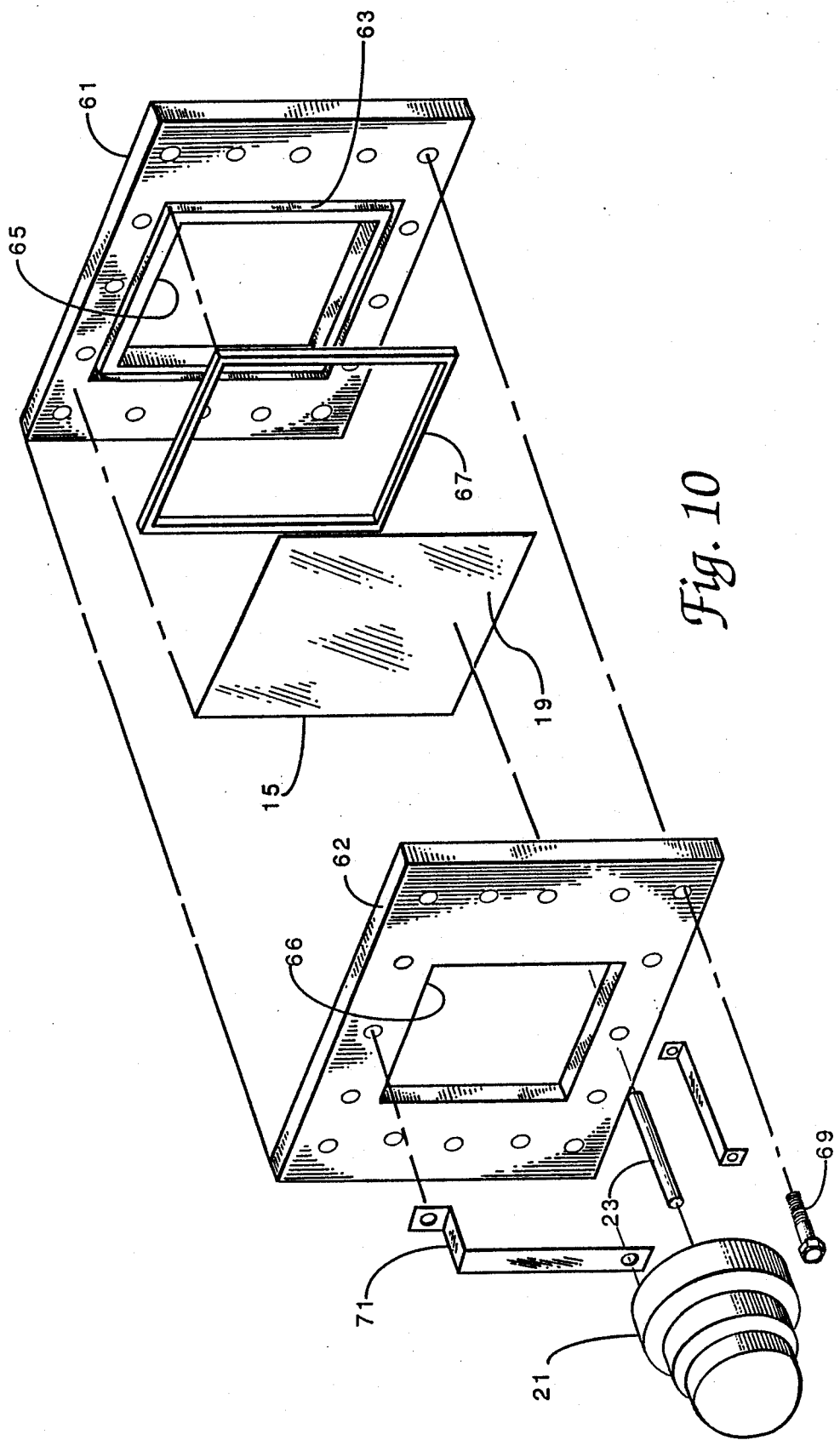

REFLECTIVE MEMBRANE OPTICAL SCINTILLATOR

RIGHTS OF THE GOVERNMENT

The invention described herein may be manufactured and used by or for the Government of the United States for all governmental purposes without the payment of any royalty.

BACKGROUND OF THE INVENTION

The present invention relates generally to systems and methods for imitating the optical state of the atmosphere and more particularly to an optical scintillation system for simulating optical atmospheric turbulence.

Evaluation techniques for optical receivers existing prior to this invention required both laboratory and field testing in order to correlate receivers to atmospheric scintillation effects. Substantial prior work on the statistical behavior of atmospheric scintillation has provided a substantial data base of probability densities and distributions and power spectral densities of spatial distribution patterns of laser and non-laser sources for a variety of sources, atmospheric conditions and regional locale. However, testing of optical receivers is often needed under specific scintillation conditions, suitable statistical control over which is not always possible. A reliable laboratory instrument capable of spatially modulating collimated lght to simulate atmospheric turbulence conditions was therefore needed. Prior attempts to simulate atmospheric scintillation using fluid tanks and thermal heating of air failed to produce a device providing reproducible results which are both wavelength independent and statistically programmable in real time.

The invention provides a system for performing the function just described and which offers real-time statistical and wavelength independent control over the spatial intensity modulation of light sources used for laboratory analysis of optical receivers and provides realistic simulation of effects of optical atmospheric turbulence on laser and non-laser sources in order to minimize or eliminate requirements for extensive field testing of optical receivers. Acoustic energy coupled to a bounded reflective membrane through an electromechanical transducer sets up nodal vibrational modes in the membrane, creating angular distortion areas which redistribute energy in the reflected beam. Collimated light reflected off the membrane surface is spatially modulated in a manner which simulates effects observed over long path propagation through the atmosphere.

It is therefore a principal object of the invention to provide an optical scintillation system for simulating optical atmospheric turbulence effects.

It is a further object of the invention to provide a system for statistical programmability of atmosphere turbulence effects.

It is yet another object of the invention to provide an optical scintillation system for simulating long path propagation of a light beam through the atmosphere.

These and other objects of the invention will become apparent as the detailed description of representative embodiments proceeds.

SUMMARY OF THE INVENTION

In accordance with the foregoing principles and objects of the invention, a reflective membrane optical scintillator system for laboratory simulation of atmospheric laser scintillation is described which comprises a substantially rigid frame defining an opening of preselected size and shape, a reflective membrane stretched on the frame within the opening and held to provide a well defined boundary for vibrational excitation of the membrane, a source of light and related optics for directing a collimated light beam onto the membrane, and an acoustic transducer for controllably vibrationally exciting the membrane with a preselected acoustical spectrum for spatially modulating the beam whereby atmospheric turbulence effects are predictably simulated

DESCRIPTION OF THE DRAWINGS

The invention will be more clearly understood from the following detailed description of representative embodiments thereof read in conjunction with the accompanying drawings wherein:

FIG. 5 is a plot of monotone excitation frequency versus cell size of reflected radiance for a typical membrane used to generate the FIG. 3,4 patterns;

FIG. 7a is a power density spectrum of the input to the transducer compared to that of FIG. 7b showing the corresponding scintillated output of the invention for a typical membrane;

FIG. 10 is a perspective view of a mount for the membrane of the invention defining the vibrational boundary thereof.

DETAILED DESCRIPTION

Figures 1, 1A:
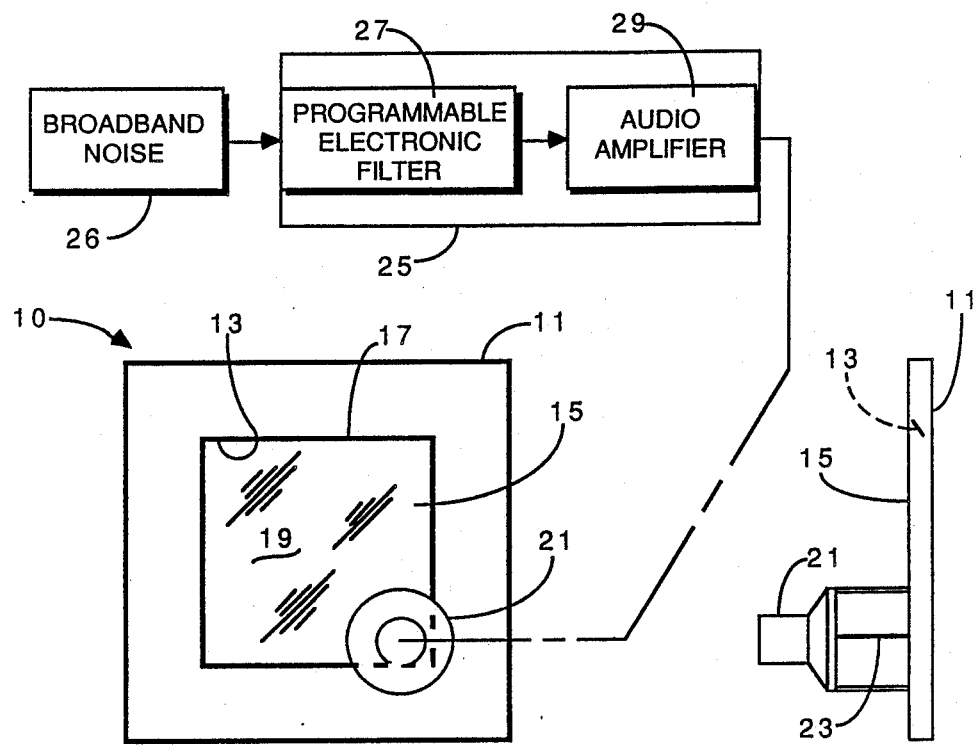
FIG. 1 is a schematic illustration of the reflective membrane optical scintillator device of the invention together with a block diagram illustrating operating logic and associated electronics.
FIG. 1a is a side view of the device of FIG. 1.

Referring now to the drawings, FIG. 1 shows schematically the reflective membrane optical scintillator device 10 of the invention together with a block diagram illustrating operating logic and associated electronics for the operation of device 10. FIG. 1a is a side view of device 10. Device 10 comprises a rigid frame 11 defining an opening 13 over which is stretched a thin reflective membrane 15. Membrane 15 is held in a tightly stretched condition over opening 13 by suitable mechanical or adhesive means 17 on frame 11 which provides a well defined mechanical boundary for acoustical excitation of membrane 15 in the practice of the invention as hereinafter described. Membrane 15 may comprise suitable film of plastic or the like, such as Mylar TM or other polymers having thickness of from about 0.025 to 0.25 millimeters. The peripheral shape of the mechanical boundary defining an excitable surface area 19 of membrane 15 may have substantially any geometry. However, the practiced form of the invention utilizes a rectangular mechanical boundary as shown in FIG. 1. Considering that the wave equation describing the vibrational characteristics of membrane 15 has a closed analytic solution for only a few simple boundary conditions, namely circles and rectangles, a monotonic relationship of excitation frequency and scintillation cell size is more easily realizable. Membrane 15 may generally range in overall size from about 100 to 500 square centimeters, a membrane selected for a system built in demonstration of the invention being rectangular (20×24 cm). Surface 19 may have a thin optically reflective coating of silver, aluminum or other single or multi layered metallic or other optical coating providing a wavelength independent reflective surface on membrane 15. An electromechanical acoustic transducer 21 having a frequency response of from about 1 Hz to 5 KHz (such as a loud-speaker driver mechanism) is mounted to frame 11 with the acoustic drive means of transducer 21, represented in FIG. 1a by rigid push rod or piston 23, in contact with membrane 15. Acoustic energy may therefore be coupled into membrane 15 from transducer 21 through piston 23.

Figure 2A:
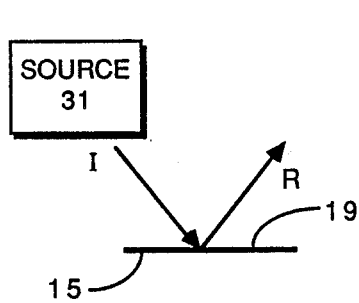
FIG. 2a illustrates incident and reflected light beams from an unexcited membrane of the FIG. 1 device.
Figure 2B:
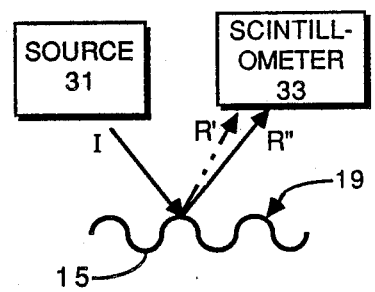
FIG. 2b illustrates incident and reflected light beams from an excited membrane of the FIG. 1 device.
Figure 4:
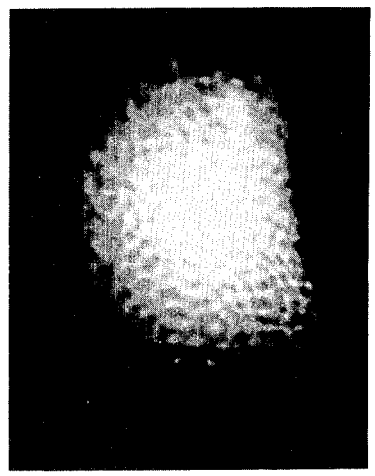
FIG. 4 shows a high speed photograph of a typical stationary pattern produced by high frequency monotone excitation of the membrane used to produce the FIG. 3 pattern.
Figure 2C:
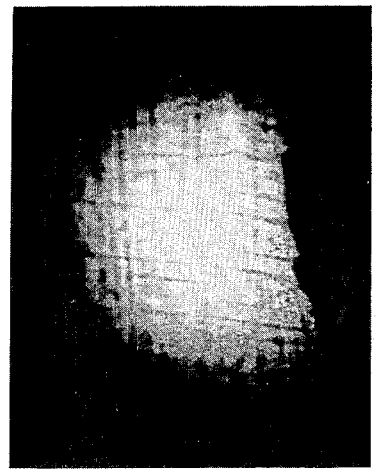
FIG. 2c shows a high speed photograph of a typical pattern produced by laser light reflected from an unexcited membrane.
Figure 3:
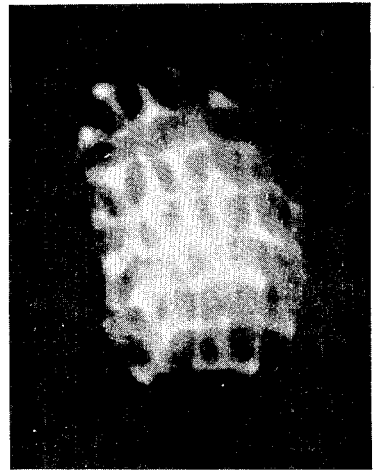
FIG. 3 shows a high speed photograph of a typical stationary pattern produced by low frequency monotone excitation of a rectangular membrane.

As suggested above, reflective membrane optical scintillator device 10 is configured to reflect and spatially modulate a light beam in such manner to simulate effects observed over long path propagation of the light beam through the atmosphere. Controllable excitation of membrane 15 may be achieved utilizing suitable electronics 25 including programmable electronic filter 27 and amplifier 29. Electronic signals in the 1 Hz to 5 KHz range presented to transducer 21 set up nodal vibrational modes in bounded membrane 15, which generate angular distortion areas along surface 19. Referring now to FIGS. 2a and 2b, illustrated therein are, respectively, an unexcited membrane 15 with incident and reflected beams I,R from an appropriate light source 31 and the excited membrane 15 with incident beam I and the distribution of reflected beams R',R" characteristic of the excitation of membrane 15. The excitation of membrane 15 as suggested in FIG. 2b generates distortion areas in surface 19 which reflect incident beam I and predictably change the spatial irradiance distribution of beam R. The statistics of the energy distribution of reflected beams R',R" depend on the acoustical spectrum applied to transducer 21 and of the shape and impedance of boundary conditions imposed on membrane 15. For single frequency (monotone) excitation of membrane 15, device 10 produces spatially distributed reflected beams R',R" in the form of stationary cells of generally uniform size and predictable distribution. Referring now to FIGS. 3 and 4, shown therein are high speed photographs (1/1000th of a second) of typical stationary patterns produced respectively by low frequency monotone and high frequency monotone excitation of a rectangular membrane 15 of Mylar TM 0.1 mm thick with silvered reflective surface 19. By comparison, FIG. 2c shows a high speed photograph of a typical pattern produced by laser light reflected from an unexcited membrane 15. The uniform light and dark cells characteristic of low frequency (820 Hz) monotone excitation in the use of device 10 are evident in FIG. 3, and the pattern generated by high frequency (2000 Hz) monotone excitation of the same membrane is illustrated in FIG. 4. Referring now to FIG. 5, shown therein is a plot of input (excitation) frequency (Hz) versus spatial cell size (mm) of reflected radiance for the same membrane 15 used to generate the FIG. 3,4 patterns. In the course of demonstrating the function and utility of the invention, a one-to-one relationship between excitation frequency and cell size was demonstrated.

Figure 6:
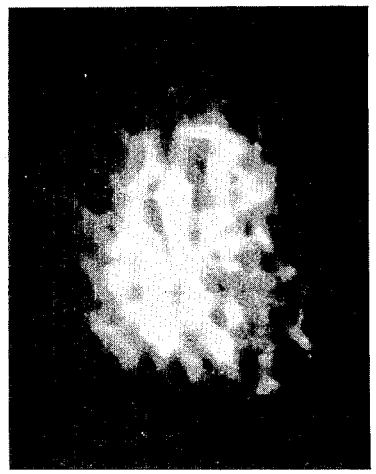
FIG. 6 is a high speed photograph of random frequency excitation, nonstationary irradiance fluctuations simulating a naturally scintillated laser.

The principal mode of operation is not the monotone excitation mode described above, however, but rather a random excitation mode hereinafter described. Referring now to FIG. 6, shown therein is a photograph of a pattern generated by a band of random frequency (500 to 2000 Hz) excitation of membrane 15 producing nonstationary irradiance fluctuations simulating a naturally scintillated laser. In FIG. 7a shows the power density spectrum of input to transducer 21 of the demonstration system which is compared to FIG. 7b showing the corresponding scintillated output of device 10, which characterizes a system transfer function not unlike that of simulating long path propagation of a light beam through the atmosphere in accordance with a stated purpose of the invention.

Figure 8:
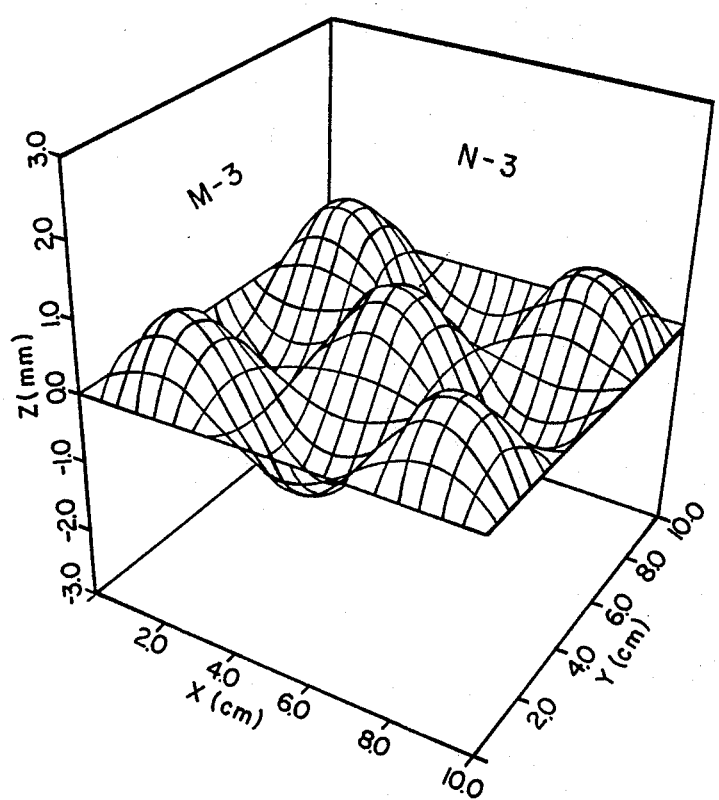
FIG. 8 shows a typical vibration mode for a square membrane.

Vibrating membranes such as membrane 15 exhibit preferred vibration modes as functions of boundary geometry, acoustic impedance, amplitude of modulation and driving frequency. Circular membrane resonances are center oriented and oscillation cells are nonuniform in size whereas rectangular membrane resonances exhibit substantially uniform scintillation cells and the acoustic impedance at the boundary interface significantly influences resonance conditions. FIG. 8 illustrates the motion of a square membrane in one $(n=3, m=3)$ of the many possible vibration modes. Cell sizes are uniform and evenly distributed across the surface and the many local deflections can redistribute the cross-sectional intensity of a laser beam reflected from the wavy surface. Resonant vibrations produce the largest surface deflections and generate the best intensity depth of modulation. Amplitude of the electronic noise signal directly impacts surface deflection. Driving frequency controls size of the oscillating cell; high frequencies produce small cells and low frequencies produce large cells. Control over cell size is an important advantage since experimental observations have shown that variations in scintillation cell size do occur in nature.

In work preformed in demonstration of the invention, spatial distribution measurements were made using a scintillometer 33 specially constructed to measure the statistics of atmospheric scintillation. The principal measurement products of the scintillometer measurement are probability distributions of spatial scintillation cell sizes, used to quantify atmospheric scintillation effects. With reference again to FIG. 1, noise from a broadband electrical noise generator 26 is electronically filtered at 27 to tailor the distribution of the acoustical excitation produced by electronics 25. Filter 27 is programmed to produce a desired statistical behavior. Amplifier 29 provides the necessary gain to drive transducer 21 to modulate membrane 15.

The transfer function relating an input audio spectrum to the spatial distribution may be determined either analytically, empirically or heuristically. Fluctuation in scintillated beam irradiance is statistically expressed through a probability density function. Variations in irradiance incident on scintillometer 33 are correlated to frequency of occurrence and the resulting histogram transformed into a normalized semilogarithmic form.

Figure 9:
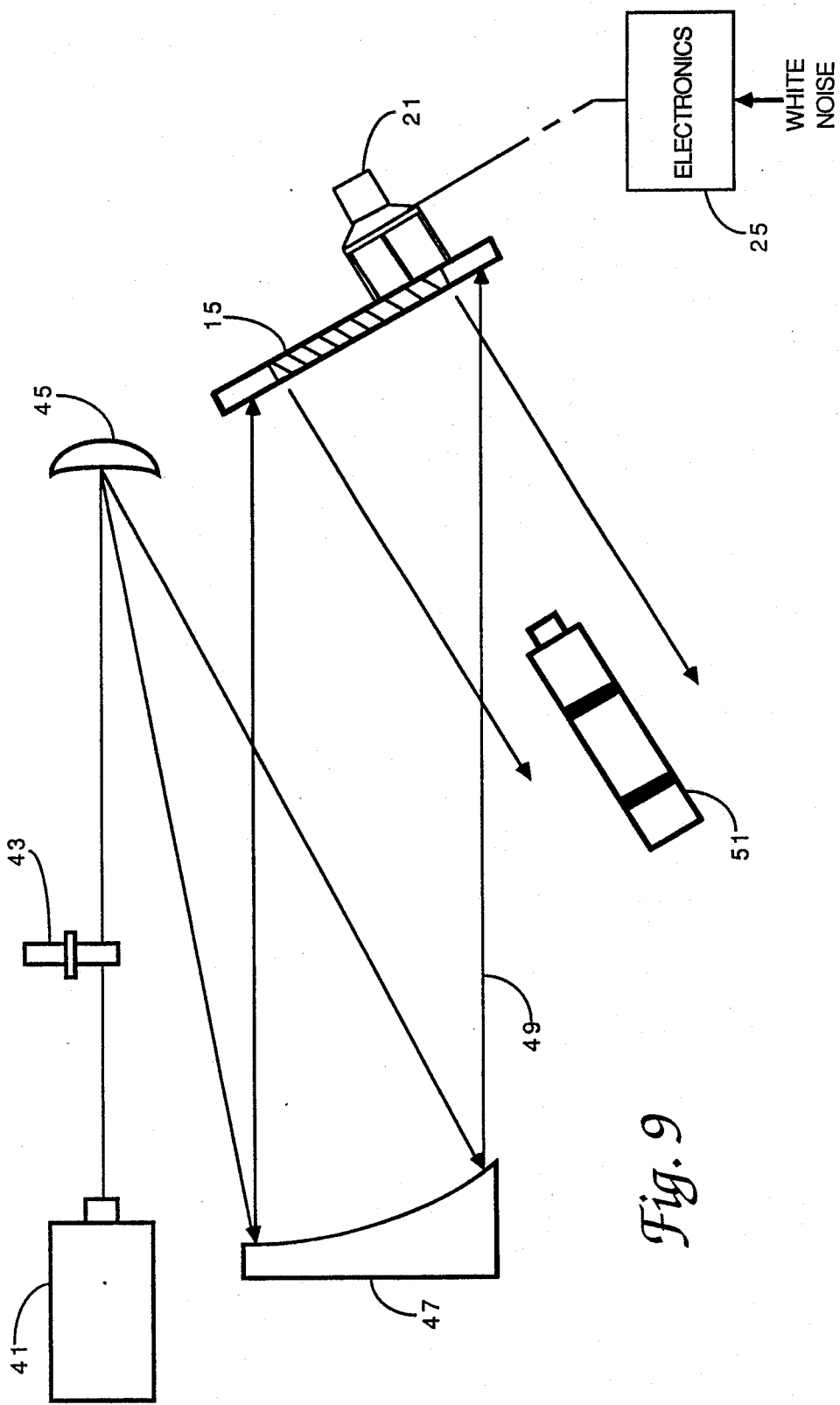
FIG. 9 is a schematic of a practical system for practicing the invention.

A typical arrangement of the invention in an optical receiver test is shown in FIG. 9. Laser light from such as argon laser 41 transmitted through a circular neutral density attenuator 43 is expanded using a suitable expanding mirror 45 and recollimated at a larger diameter mirror such as off-axis paraboloid mirror 47. The expanded beam 49 is reflected from modulated membrane 15 into optical receiver 51 under test spaced a preselected distance (about 2 meters) from membrane 15. White noise is applied to transducer 21 in manner described above in relation to FIG. 1. Probability distribution statistics are measured by replacing optical receiver 51 in FIG. 9 with scintillometer 33 (FIG. 2b).

Referring now to FIG. 10, shown therein is a highly useful and functional mounting arrangement for membrane 15 of the invention. A metallized Mylar ™ membrane 15 is sandwiched between two 6 mm thick aluminum plates 61,62 each of which have an "O" ring groove 63 (shown on plate 61 only) cut into each inward facing side adjacent membrane 15. Each groove is cut about 3 mm from the respective openings 65,66 defined in plates 61,62 for framing membrane 15 and defining surface 19 thereof for excitation according to the governing principles of the invention. Plates 61,62 with membrane 15 and "O" ring 67 therebetween may be bolted together utilizing bolts 69. The assembly of plates 61,62 as shown results in "O" ring 67 pulling membrane 15 outwardly which results in a mirror like optical surface much superior to that attainable using heat shrinkage techniques. Transducer 21 with piston 23 may be attached to plate 62 substantially as shown using such as bracket 71. The principal benefits of the two plate construction of FIG. 10 is reliable membrane 15 attachment, refined boundary geometry and impedance conditions, and improved optical surface quality without changes in functioning of the invention as described above.

Figure 11B:
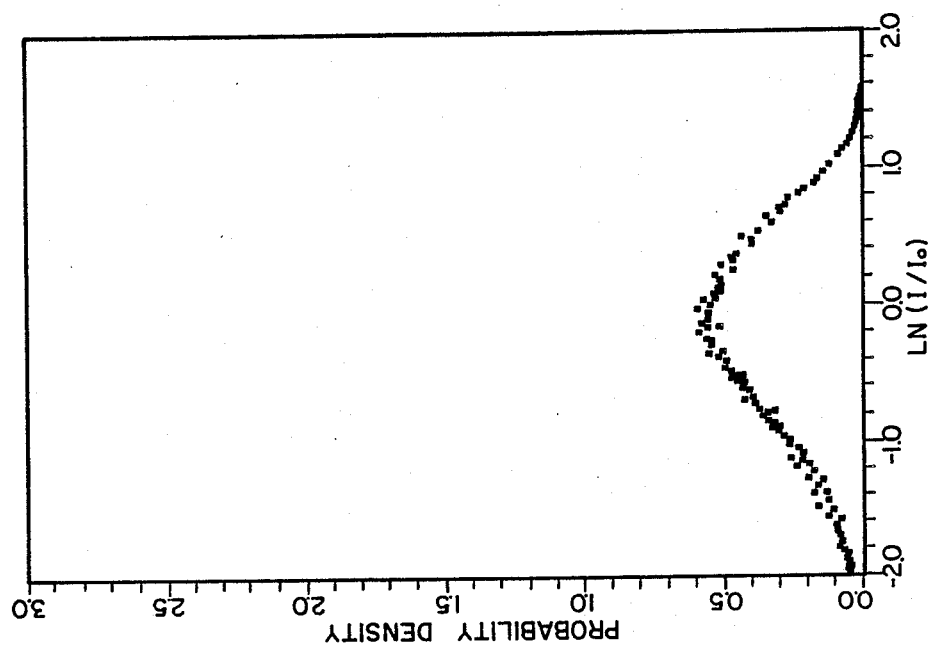
FIGS. 11a, 11b show log-normal probability density functions generated in demonstration of the invention for weak turbulence and strong turbulence, respectively.
Figure 11A:
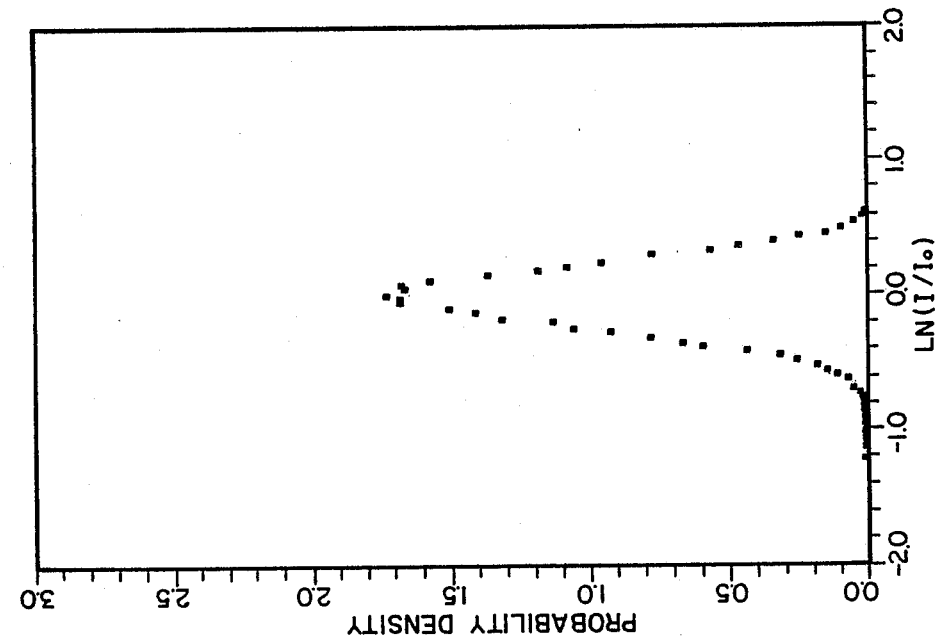
Figure 12B:
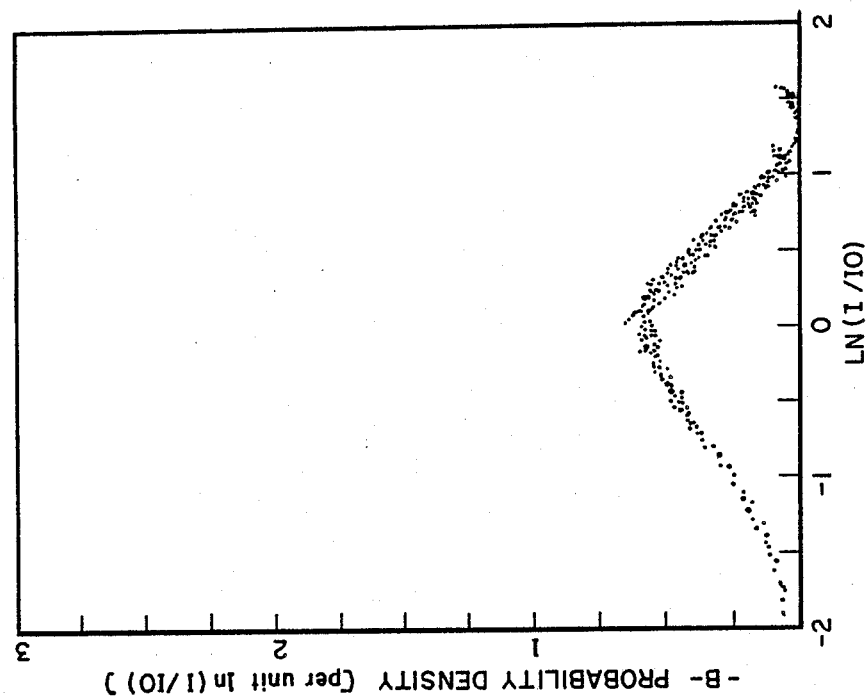
FIGS. 12a, 12b show actual field test data on naturally scintillated laser light for weak turbulence and strong turbulence, respectively.
Figure 12A:
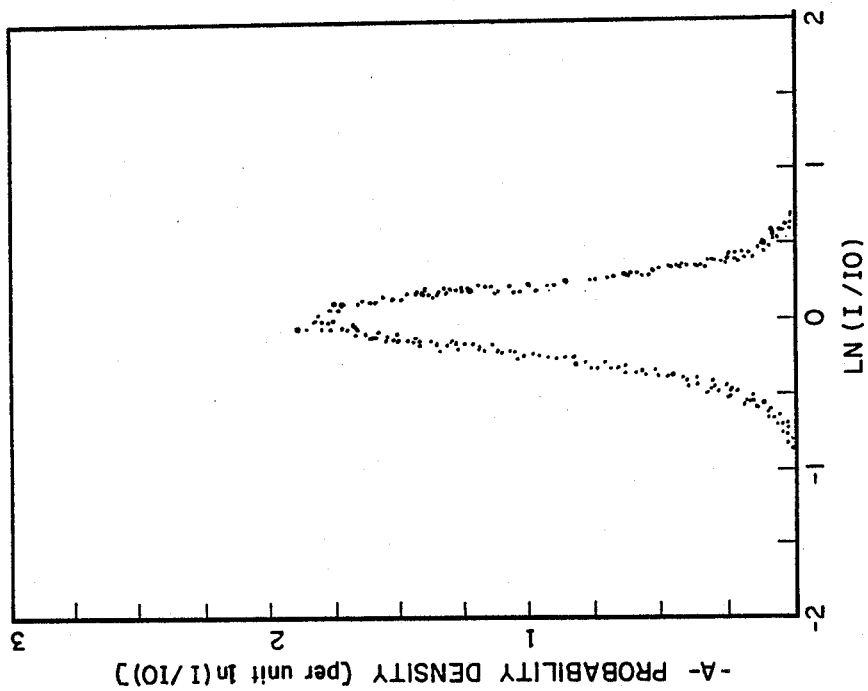

Measurements made on the scintillated field in demonstration of the invention reveal that log normal probability distributions can in fact be generated by appropriate filtering of membrane driving frequencies. FIGS. 11a, 11b show log-normal probability density functions generated in demonstration of the invention for weak turbulence and strong turbulence, respectively. FIGS. 12a, 12b show actual field test data on naturally scintillated laser light for weak turbulence and strong turbulence, respectively. The probability density versus intensity graphs of FIGS. 11a, 11b, compare well with actual field-test data shown in FIGS. 12a, 12b. Variance was found to be a function of white noise peak-to-peak amplitude and working distance from membrane 15.

The invention therefore provides a reflective membrane optical scintillator for imitating atmospheric optical turbulence effects. It is understood that modifications to the invention as described may be made as might occur to one skilled in the field of the invention within the scope of the appended claims. All embodiments contemplated hereunder which achieve the objects of the invention were therefore not shown in complete detail. Other embodiments may be developed without departing from the spirit of the invention or from the scope of the appended claims.

We claim:

1. An optical scintillation system for simulating optical atmospheric turbulence effects, comprising:
   (a) a substantially rigid frame defining an opening of preselected size and shape;
   (b) a membrane stretched on said frame within said opening, said membrane supporting a reflective surface;
   (c) means for holding said membrane on said frame and providing a well defined boundary for vibrational excitation of said membrane;
   (d) a source of light and optical means for directing a collimated light beam onto said membrane; and;
   (e) acoustic means for controllably vibrationally exciting said membrane with a preselected acoustical spectrum for spatially modulating said light beam whereby atmospheric turbulence effects are predictably simulated.

2. The system of claim 1 wherein said acoustic means comprises an acoustic transducer.

3. The system of claim 1 wherein said membrane comprises a thin film of a material selected from the group consisting of plastic, Mylar ™, metallized Mylar ™, and metallized plastic.

4. The system of claim 3 wherein said thin film has thickness of from about 0.025 to 0.25 millimeters.

5. The system of claim 1 wherein said means for holding said membrane on said frame defines a rectangular peripheral boundary for vibrational excitation of said membrane.

6. The system of claim 1 further comprising a metallic coating on said membrane, said metallic coating defining said reflective surface.

7. The system of claim 6 wherein said metallic coating comprises a metal selected from the group consisting of silver and aluminum.

8. The system of claim 1 wherein said source of light is coherent.

* * * * *